United States Patent
Sharrock et al.

(10) Patent No.: US 7,317,532 B2
(45) Date of Patent: *Jan. 8, 2008

(54) FLOW SENSING FOR DETERMINATION OF ASSAY RESULTS

(75) Inventors: Stephen P. Sharrock, Bedford (GB); Andrew P. Phelan, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/742,459

(22) Filed: Dec. 19, 2003

(65) Prior Publication Data

US 2005/0037511 A1 Feb. 17, 2005

Related U.S. Application Data

(60) Provisional application No. 60/508,001, filed on Oct. 2, 2003.

(30) Foreign Application Priority Data

Jun. 4, 2003 (GB) .................................. 0312801.4

(51) Int. Cl.
G01N 21/00 (2006.01)
(52) U.S. Cl. ........................................ 356/436; 356/27
(58) Field of Classification Search ................ 356/436, 356/433, 446, 448, 39, 27, 445
See application file for complete search history.

(56) References Cited

U.S. PATENT DOCUMENTS 3,941,477 A * 3/1976 Schodl ........................ 356/28
4,399,362 A 8/1983 Cormier et al.
4,420,566 A 12/1983 Jessop et al.
4,523,853 A 6/1985 Rosenbladt et al. ........ 356/446
4,676,653 A 6/1987 Strohmeier et al. ........ 356/446

(Continued)

FOREIGN PATENT DOCUMENTS

DE 196 28 562 1/1998

(Continued)

OTHER PUBLICATIONS

Search Report dated Dec. 1, 2003 for GB 0312815.4.

(Continued)

Primary Examiner—Gregory J. Toatley, Jr.
Assistant Examiner—Kara Geisel
(74) Attorney, Agent, or Firm—Scott E. Kamholz; Foley Hoag LLP (57) ABSTRACT

An assay result reading device for reading the result of an assay performed using a liquid transport carrier may include at least one light source capable of emitting light incident upon at least one of two or more spatially separated zones of the carrier, a photodetector so positioned as to be capable of detecting light emanating from each of the two said zones and generating signals representing the presence or absence of a fluid sample in the respective zone, and a computation circuit. The computation circuit may be responsive to the signals to calculate a flow rate for a fluid flowing along the carrier, compare the calculated flow rate to upper and lower limits, and reject the assay result if the calculated flow rate is outside the upper and lower limits.

27 Claims, 7 Drawing Sheets

U.S. PATENT DOCUMENTS

| | | |
|---|---|---|
| 4,995,402 A | 2/1991 | Smith et al. |
| 5,049,487 A | 9/1991 | Phillips et al. |
| 5,114,350 A | 5/1992 | Hewett |
| 5,145,789 A | 9/1992 | Corti et al. |
| 5,304,468 A | 4/1994 | Phillips et al. ............... 435/14 |
| 5,344,754 A | 9/1994 | Zweig |
| 5,504,013 A | 4/1996 | Senior |
| 5,580,794 A | 12/1996 | Allen ........................ 436/169 |
| 5,679,584 A | 10/1997 | Mileaf et al. |
| 5,786,220 A | 7/1998 | Pronovost et al. |
| 5,837,546 A * | 11/1998 | Allen et al. ................. 436/169 |
| 5,885,839 A | 3/1999 | Lingane et al. |
| 5,889,585 A * | 3/1999 | Markart ........................ 356/39 |
| 5,968,835 A | 10/1999 | Aoki et al. ................. 436/110 |
| 5,968,839 A | 10/1999 | Blatt et al. |
| 6,055,060 A | 4/2000 | Boldnau et al. ........... 356/433 |
| 6,156,271 A | 12/2000 | May |
| 6,194,222 B1 | 2/2001 | Buechler et al. ............ 436/518 |
| 6,235,241 B1 | 5/2001 | Catt et al. .................... 422/56 |
| 6,361,956 B1 | 3/2002 | Hanninen et al. |
| 6,399,398 B1 | 6/2002 | Cunningham et al. |
| 6,448,067 B1 * | 9/2002 | Tajnafoi ................. 435/288.7 |
| 6,454,726 B1 | 9/2002 | Catt et al. |
| 6,707,554 B1 | 3/2004 | Miltner et al. .............. 356/433 |
| 6,825,918 B2 | 11/2004 | Eisenmann et al. ........... 356/39 |
| 6,949,221 B2 | 9/2005 | Kiser et al. |
| 6,951,631 B1 | 10/2005 | Catt et al. .................... 422/56 |
| 7,018,847 B2 | 3/2006 | Mendel-Hartvig et al. |
| 7,109,042 B2 | 9/2006 | May et al. |
| 2002/0192833 A1 * | 12/2002 | Pan et al. .................... 436/164 |
| 2003/0180815 A1 | 9/2003 | Rawson et al. .............. 435/7.9 |
| 2004/0152208 A1 | 8/2004 | Hutchinson ................. 436/518 |
| 2004/0152209 A1 | 8/2004 | Zin et al. .................... 435/518 |

FOREIGN PATENT DOCUMENTS

| | | |
|---|---|---|
| EP | 0653625 | 11/1994 |
| EP | 0 728 309 B1 | 8/1997 |
| EP | 0 826 777 A1 | 3/1998 |
| EP | 0833145 | 4/1998 |
| GB | 2365526 | 7/2000 |
| WO | WO 1998/025143 A1 | 6/1998 |
| WO | WO1999/35602 | 7/1999 |
| WO | WO2004/070353 | 8/2004 |

OTHER PUBLICATIONS

European Search Report dated Jul. 3, 2006 for EP 04 25 3076.
Search Report dated Jul. 3, 2006 for FR 0406067.
Search Report dated Dec. 1, 2003 for GB0312801.4.
European Search Report dated Jul. 11, 2006 for EP 04 25 3077.
Search Report dated Jul. 11, 2006 for FR 0406065.
Search Report dated Dec. 1, 2003 for GB 0312802.2.
European Search Report dated Jul. 14, 2006 for EP 04 2503078.
Search Report dated Jul. 14, 2006 for FR0406066.

\* cited by examiner

FLOW SENSING FOR DETERMINATION OF ASSAY RESULTS

CROSS-REFERENCE TO RELATED APPLICATION

This application claims the benefit of U.S. Provisional Patent Application Ser. No. 60/508,001, filed Oct. 2, 2003, the entire contents of which are hereby incorporated herein by this reference.

FIELD

The disclosed subject matter relates to assay reading devices for the measurement of analytes. In particular it relates to electronic readers for use with assay test-strips which use optical methods of flow measurement.

BACKGROUND

Analytical devices suitable for home testing of analytes are now widely commercially available. An immunoassay device suitable for this purpose for the measurement of the pregnancy hormone human chorionic gonadotropin (hCG) is sold by Unipath under the brand-name CLEARBLUE® and is disclosed in EP291194.

EP291194 discloses an immunoassay device comprising a porous carrier containing: a particulate labelled specific binding reagent for an analyte, which reagent is freely mobile when in the moist state; and an unlabelled specific binding reagent for the same analyte, which reagent is immobilised in a detection zone or test zone downstream from the unlabelled specific binding reagent. Liquid sample suspected of containing analyte is applied to the porous carrier whereupon it interacts with the particulate labelled binding reagent to form an analyte-binding partner complex. The particulate label is coloured and is typically gold or a dyed polymer, for example latex or polyurethane. The complex thereafter migrates into a detection zone whereupon it forms a further complex with the immobilised unlabelled specific binding reagent enabling the extent of analyte present to be detected or observed. Due to the nature of the binding reactions taking place it is necessary to wait for a particular period of time to elapse after the test has commenced in order to read the result. This is particularly important for a visual, semi-quantitative type of test whereby the detection zone or read line develops over time.

Various methods of timing the result have been proposed for commercial devices, including instructions to the user wait for a particular length of time before reading the assay result. Other methods include a signal that is generated after a particular period of time has elapsed, as disclosed in our copending application no. PCT/EP03/00274 which signal informs the user that the assay result should now be read.

As a control and to ensure the correct functioning of the device, a control zone is generally provided downstream from the measurement zone. A third binding reagent, which is able to bind with the first labelled reagent, is immobilised at this control zone such that in the absence of analyte, the user will be able to check if the test has been carried out correctly.

EP653625 discloses a lateral flow assay test-strip for use in combination with an assay reader whereby the extent of binding of particulate label is determined optically. It is also known from U.S. Pat. No. 5,580,794 to provide an integrated assay device and lateral flow assay test-strip wherein the result is determined optically using reflectance measurements.

U.S. Pat. No. 5,837,546 discloses a method of automatically starting an immunoassay device whereby a lateral flow carrier is provided with additional electrodes which sense the presence of fluid on the test-strip and a signal is generated which switches on the sensing electronics.

Due to the nature of a lateral flow type test which requires the release of a labelled particulate binding reagent, flow of liquid along a carrier (typically porous) and capture of the analyte complex in the detection zone, it is desirable to optimise the properties of the porous carrier.

The pore size of the carrier is an important consideration and is preferably chosen to be between 1–12 µm. The carrier is conveniently nitrocellulose, the pore size of which may vary in part due to the manufacturing process. The assay device may additionally have a wick in fluid communication with the carrier which serves to collect the liquid sample and the carrier typically comprises two pieces of different materials. Nitrocellulose is typically used as the carrier material for the assay strip and has considerable advantages over conventional strip materials, such as paper, because of its natural ability to bind proteins without requiring prior sensitisation. In order to optimise the assay, the nitrocellulose is typically subjected prior to use to a number of treatments which include the use of blocking agents such polyvinylalcohol and the use of soluble glazes such as sugar to enhance release of the labelled reagent.

The present inventors have observed that the flow rate of fluid along the porous carrier may vary from test to test. In some cases the carrier has a tendency to flood, i.e. the fluid front moves along the carrier at a faster rate than normal. Conversely, in some cases, it has been noted that the fluid front moves along the carrier at a much slower rate than normal, namely the carrier is blocked to some extent. It has been found that these different types of fluid flow-rate behaviour can give rise to inaccurate results.

Due to the inconsistent nature of the materials used for both the wick and the porous membrane, the optimum point in time (after application of the liquid sample) for reading the result can be variable.

In the interests of providing devices which are inherently more accurate and reliable, it would be desirable to provide alternative or additional control features which would be able to determine the extent and/or rate at which the liquid sample moved along the porous carrier and to reject those readings where the flow rate was determined to fall outside of predetermined limits.

It would also be desirable to provide a method wherein the optimum time for reading the result could be reliably and reproducibly determined.

SUMMARY

The present disclosure provides, in some embodiments, an assay device comprising a reader for use in conjunction with a lateral flow test-strip which is able to optically measure analyte concentrations quantitatively and/or qualitatively with a high degree of reliability and accuracy.

The present disclosure also provides an assay reader, especially one for use in conjunction with a lateral flow test-strip, as well as a method of performing an analyte measurement, wherein the extent and/or rate of fluid flow along the test strip may be determined and wherein the final assay result may be rejected where the fluid flow rate has been determined to fall outside of certain predetermined limits.

In some embodiments, an assay result reading device for reading the result of an assay performed using a liquid transport carrier includes at least one light source capable of emitting light incident upon at least one of two or more spatially separated zones of the carrier, a photodetector so positioned as to be capable of detecting light emanating from each of the two said zones and generating signals representing the presence or absence of a fluid sample in the respective zone and a computation circuit responsive to the signals to calculate a flow rate for a fluid flowing along the carrier, compare the calculated flow rate to upper and lower limits, and reject the assay result if the calculated flow rate is outside the upper and lower limits.

In some embodiments, a method of performing an assay for an analyte of interest in a liquid sample includes positioning a liquid transport carrier in relation to an assay result reader, the carrier having at least two spatially-separated zones, the reader comprising a housing enclosing at least one light source and at least one photodetector, and the carrier positioned so that the at least one light source emits light incident on at least one of the zones, and so that light emanating from at least one of the zones is incident on the photodetector; applying or introducing the liquid sample to the liquid transport carrier; calculating a flow rate of the liquid sample along the carrier in response to signals generated by the at least one photodetector representing the presence or absence of the liquid sample in a respective zone; and determining whether the calculated flow rate is within predetermined acceptable limits.

The liquid transport carrier preferably comprises a porous carrier, such as a lateral flow assay test strip of the sort which are well known to those skilled in the art. Alternatively the liquid transport carrier may comprise a capillary fill chamber, channel or the like (e.g. as disclosed in U.S. Pat. No. 6,113,855). The liquid transport carrier may be an integral part of the assay result reading device e.g. in the manner disclosed in U.S. Pat. No. 5,580,794. In such an embodiment the combined reading device/liquid transport carrier would typically be disposable. Alternatively the liquid transport carrier may be a separate component, which is normally introduced into the assay result reading device during the course of performing an assay. In this latter embodiment, the liquid transport carrier (typically a lateral flow assay test strip) would generally be cheap and disposable after a single use, whilst the assay result reading device would be reusable and relatively expensive.

DETAILED DESCRIPTION

For the avoidance of doubt, it is expressly stated that any of the features described herein as "preferred", "desirable", "convenient", "advantageous" or the like may be adopted in an embodiment in combination with any other feature or features so-described, or may be adopted in isolation, unless the context dictates otherwise.

In describing the various embodiments, a number of terms are defined as follows:

"Fluid sample" refers to any liquid material suspected of containing the analyte of interest. Such samples may include human, animal or man-made samples. Typically, the sample is an aqueous solution or biological fluid.

Examples of biological fluids include urine, blood, serum, plasma, saliva, interstitial fluid and so on. Other samples which can be used include water, food products, soil extracts and the like for the performance of industrial, environmental, or food production assays as well as medical diagnostic assays. In addition, a solid material suspected of containing the analyte can be used as the test sample once it is modified to form a liquid medium which may include further treatment in order to release the analyte.

Any suitable analyte or analytes of interest may be measured. Analytes that are particularly of interest include proteins, haptens, immunoglobulins, hormones, polynucleotides, steroids, drugs, infectious disease agents (e.g. of bacterial or viral origin) such as *Streptococcus, Neisseria* and *Chlamydia*, drugs of abuse, and biological markers such as cardiac markers and so on.

Typically the disclosed assay result reading devices and methods are adapted to perform a diagnostic assay i.e. to provide information about the health status of a mammalian (typically a human) individual subject.

It is preferred to calculate the rate of progress of the liquid sample (rather than the extent thereof) along the liquid transport carrier.

Conveniently the flow rate is calculated between two zones on the liquid transport carrier, such that the presence of the liquid sample at, or passage thereof through, a first, upstream zone is detected, and likewise the present of the liquid sample at, or passage through, a second, downstream zone is detected. If the distance between the two zones is fixed and/or known, the relative or absolute flow rate of the liquid sample can be readily calculated by measuring the amount of time which elapses between detection of the liquid sample at the first and second zones.

In principle, the first and second zones may be anywhere on the liquid transport carrier so, for example, the first zone could be at the extreme upstream end and the second zone could at the extreme downstream end. The distance between the two zones (and therefore the time travel of fluid sample) may be chosen to be any that is convenient and is likely to depend upon the nature of the analyte to be determined and the physical dimensions and characteristics of the liquid transport carrier. For example the liquid transport carrier may comprise one or more microfluidic channels optionally containing one or more various microfluidic elements such as a red-blood cell separation means, time-gates, or fluid rate controlling means, all of which will influence the rate of travel of sample. In practice, it is desirable that the two zones are at a separation such that, at normal flow rates, a sufficiently accurate flow rate may be calculated within the time frame of the assay, so as not to delay the assay process or assay result determination. For an assay for the detection and/or quantification of the pregnancy hormone hCG, for example, a desirable time would be between 5 and 60 seconds.

Advantageously the presence of the liquid sample at, or passage through, one or more additional zones on the liquid transport carrier is detected. This allows for a more accurate calculation of the flow rate. A larger number of flow rate calculation zones may be advantageous when the acceptable range of flow rates is rather narrow, or where the flow rate may vary at different portions of the liquid transport carrier (e.g. where there are portions with different flow characteristics, for instance, due to the incorporation of microfluidic elements).

In addition the provision of a plurality of "check zones" allows for checking that the liquid sample progresses through each of the zones in the expected sequence, thereby alerting the user to an abnormal flow pattern if the liquid sample is detected at a downstream zone in advance of detection at a particular upstream zone. Such abnormal flow patterns can occur for instance when a porous carrier is flooded by liquid samples ("oversampling").

If the calculated flow rate is outside of the predetermined acceptable limits, then the result of the assay may be declared invalid. Thus the flow rate calculation can act as a control feature. If the calculated flow rate is too high, due to flooding of the porous carrier (e.g. as a result of oversampling; or a result of a faulty assay device due to defects in manufacture, or damage in storage or in use) the user can be alerted and the assay result disregarded. Equally, if the calculated flow rate is too low (e.g. due to undersampling) the assay result can be disregarded. Thus, errors due to, for example, over- or undersampling, may be avoided.

In principle any property of the liquid sample could be measured in order to calculate the rate and/or extent of progress of the liquid, such as its electrical capacitance, conductivity or resistivity. The porous carrier or other liquid transport carrier may comprise a substance which undergoes a detectable change in the presence of the liquid sample. For example nitrocellulose, commonly used as a porous carrier in lateral flow assay strips, is opaque (or substantially so) when dry, but its opacity is significantly reduced upon wetting. Thus measurement or detection of the change in optical reflectance or transmissivity of a nitrocellulose carrier upon wetting by a liquid sample may be sufficient to detect the rate and/or extent of progress of the liquid sample.

Preferably the means for calculating the rate and/or extent of the progress of the liquid sample applied to the liquid transport carrier comprises an optical detection system. Such an optical detection system will typically generate one or more signals (advantageously, electrical signals) in a manner responsive to the rate and/or extent of the progress of the liquid sample. In a preferred embodiment, a suitable optical system comprises at least two light sources and at least one photodetector, or conversely at least one light source and at least two photodetectors, so as to be able to make optical measurements at least two spatially separated zones of the liquid transport carrier.

In principle the light source could be external to the assay result reader e.g. ambient light. However, this is extremely likely to introduce variation, and it is therefore greatly preferred that: (a) the assay result reading device is provided with at least one integral light source (LED's are found especially convenient in this regard); and (b) the assay result reading device is provided with a housing or casing which substantially excludes, or at least greatly restricts, ambient light from entering the interior of the reading device. For present purposes, a housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the interior space within the housing: a test strip or similar porous carrier may be inserted through the aperture so as to perform an assay.

The liquid sample per se may have an optical property (e.g. colour) which renders it amenable to optical detection and/or monitoring of its progress along the liquid transport carrier. For example, a blood sample will absorb strongly in the range 400 nm to 600 nm, due to the presence of haemoglobin. Alternatively the liquid sample may be doped, prior to application to the liquid transport carrier, with a readily detectable substance (e.g. a dye, fluorochrome or the like) which will not interfere with the performance of the assay but will facilitate detection (especially optical detection) of the rate and/or extent of the progress of the liquid sample.

In yet another arrangement, the liquid transport carrier is provided with a readily detectable substance which is transported by the liquid sample. Again, a dye, fluorochrome or the like may be suitable in this regard. The readily detectable substance may conveniently be releasably immobilised on a porous carrier or the like, so as to be released upon contact with the liquid sample. The readily detectable substance may be e.g. a coloured substance which does not interfere with the assay. In a preferred embodiment the readily detectable substance is a particulate label which is attached to a mobilizable specific binding reagent (having specific binding for the analyte), and detection of which label in a detection zone constitutes an essential feature of the assay.

The particulate label may be anything suitable for the purpose, including coloured latex, a dye sol, or particulate gold. Alternatively the particulate label may comprise a fluorophore which can be excited by an LED emitting radiation of a suitable wavelength.

The preferred optical detection system will comprise at least one light source and at least one photodetector (such as a photodiode). Preferred light sources are light emitting diodes or LED's. Reflected light and/or transmitted light may be measured by the photodetector. For the purposes of this disclosure, reflected light is taken to mean that light from the light source is reflected from the porous carrier or other liquid transport carrier onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

In one embodiment the reader comprises a housing in which is contained at least two light sources (e.g. LED's) and respective photodetectors arranged to receive light from the LED's.

One of the light sources illuminates a first, upstream zone of the liquid transport carrier and another light source illuminates a second, downstream zone of the liquid transport carrier, and respective photodetectors are provided to detected light reflected and/or transmitted from the respective zones, the amount of such light which is reflected and/or transmitted depending on whether the liquid sample (optionally together with any light-absorbing or light-emitting substance transported thereby) has reached the zone(s) in question.

In a particularly preferred embodiment the assay result reading device comprises three light sources which illuminate respective first, second and third zones of the liquid transport carrier, and the flow rate of the liquid sample between at least two of the zones is measured.

Conveniently one of the zones from which measurements are made in the calculation of the flow rate is also a zone from which measurements are made in determining the result of the assay, for example, the first zone may be a zone in which analyte-specific labelled binding reagent is immobilised if analyte is present in the sample. Such a zone may be referred to as a test zone.

Desirably one of the zones from which measurements are made in the calculation of the flow rate is also a zone from which control measurements are made for the purpose of obtaining a control value, which is used to determine if the assay has been correctly performed. Such a zone may be referred to as a control zone.

It is advantageous that there is a zone, from which measurements are made in the calculation of the flow rate, which is also a zone from which measurements are made in calibration of the assay result reader. Such a zone may be referred to as a reference zone.

It is desirable that the components of the assay reader used in the detection and/or quantification of the analyte of interest are also used in calculating the flow rate of the liquid. This confers advantages of simplicity and economy, which are especially desirable for a disposable device. In particular, a preferred assay result reader has an optical detection system for detecting the presence and/or amount of the analyte of interest, and the same optical detection system is employed to make measurements for the purpose of calculating flow rates.

In a particularly preferred embodiment the assay result reader obtains measurements from a control zone, a reference zone and a test zone, the control zone being downstream from the reference zone which is itself downstream of the test zone (i.e. the reference zone is between the test and control zones). The reference zone allows for, inter alia, measurement of an optical property (e.g. reflectance and/or transmissivity) of the liquid transport carrier when wetted (e.g. a wetted porous carrier). Conveniently results obtained from the test and control zones are normalised relative to the reference zone, and this takes into account and compensates for any variation in the optical property of the sample. This is especially important when using biological samples, such as urine, which may vary widely in composition (e.g. concentration) and therefore vary in colour or colour intensity.

The housing of the assay result reader typically comprises an aperture such that a test strip may be releasably inserted into and (preferably) engaged with the housing. The housing is designed such that ambient light reaching the interior of the reading device is kept to an absolute minimum. Desirably suitable alignment and fixing means are provided within the housing such that the test strip remains in a fixed position when inserted. The light sources are arranged in the housing such that, when the test strip has been correctly inserted, the light sources are correctly aligned with the respective zones to be measured.

The assay test strip may be any conventional lateral flow assay test strip such as disclosed in EP291194 or U.S. Pat. No. 6,352,862. The test strip preferably comprises a porous carrier containing a particulate labelled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors generate a current roughly proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP653625.

Alternatively, instead of using a test strip comprising a lateral flow porous carrier such as described by EP291194, a test strip having the binding reagents disposed within a capillary could be used, such as disclosed by U.S. Pat. No. 6,113,855.

In order to conduct an assay measurement using a assay result reading device in accordance with some of the preferred features, a test strip is inserted into the reader, and a liquid sample is then added to a sample receiving portion of the test strip. Alternatively a liquid sample may be applied to the test strip first, and the strip then inserted into the reader. The sample migrates along the porous carrier and reaches a first zone, typically the test zone. When sample is added to the strip, a coloured particulate label is resuspended and migrates along the carrier along with the fluid. As the fluid front of the sample reaches first zone, there is a reduction in light intensity reaching the photodetector since the coloured particulate label absorbs some of the light. This change in reflected or transmitted light intensity is recorded. In practice, a larger amount of the particulate label is present in the initial fluid front than in the subsequent fluid. In addition, if a binding reaction takes place in the test zone due to the presence of analyte, particulate label will tend to remain in the test zone. Thus the shape of the resultant voltage-time profile observed will depend upon whether the zone is a test, control or reference zone. For a three zone system, three voltage-time profiles will be recorded one for each zone, having a time lag due to the fact that measurement zones are spatially separated from one another and thus the time taken for the fluid front to reach the first zone is less than that taken to reach the second and so on.

From analysis of the voltage-time profiles for the respective zones and with knowledge of the distance between the zones, the rate of fluid flow may be determined. By use of a simple algorithm, the final assay reading may be rejected if the calculated flow rate has been determined to be too low or too high.

In a typical embodiment, the assay result reading device will typically further comprise one or more of the following: a central processing unit (CPU) or microcontroller; two or more LED's; two or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay. Displays suitable for displaying this sort of information are known to those skilled in the art and disclosed, for example, in WO 99/51989.

For the avoidance of doubt, it is expressly stated that any of the features described as "preferred" "desirable" "convenient", "advantageous" or the like may be adopted in combination with any other feature or features so-described, or may be adopted in isolation, unless the context dictates otherwise.

EXAMPLES

Example 1

Figure 1:
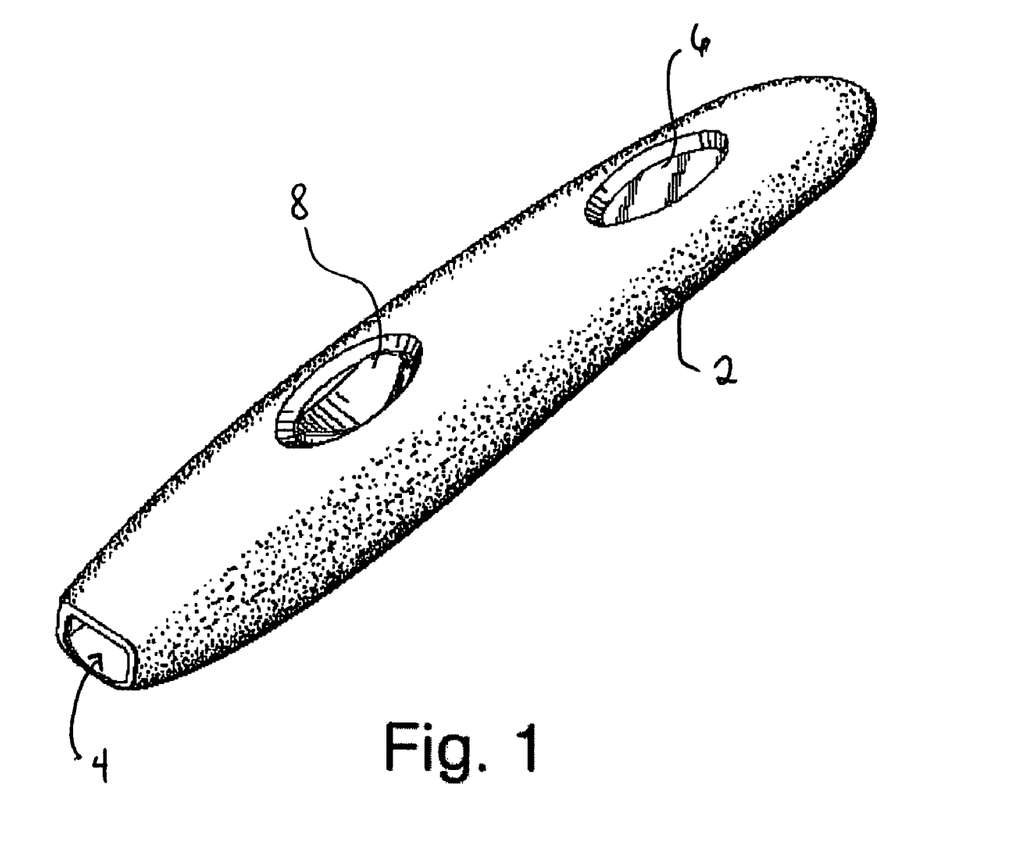
FIG. 1 is perspective view of one embodiment of an assay result reading device in accordance with the present disclosure.

An embodiment of an assay result reading device in accordance with the present disclosure is illustrated in FIG. 1.

The reading device is about 12 cm long and about 2 cm wide and is generally finger or cigar-shaped. In preferred embodiments, the housing is no larger than about 12 cm long, about 2.5 cm wide, and about 2.2 cm tall. However, any convenient shape may be employed, such as a credit card shaped reader. The device comprises a housing 2 formed from a light-impermeable synthetic plastics material (e.g. polycarbonate, ABS, polystyrene, high density polyethylene, or polypropylene or polystyrol containing an appropriate light-blocking pigment, such as carbon). At one end of the reading device is a narrow slot or aperture 4 by which a test strip (not shown) can be inserted into the reader.

On its upper face the reader comprises two oval-shaped apertures. One aperture accommodates the screen of a liquid crystal display 6 which displays information to a user e.g. the results of an assay, in qualitative or quantitative terms. The other aperture accommodates an eject mechanism 8 which, when actuated, forcibly ejects an inserted assay device from the assay result reading device.

The assay device for use with the reading device is a generally conventional lateral flow test stick e.g. of the sort disclosed in U.S. Pat. No. 6,156,271, U.S. Pat. No. 5,504,013, EP 728309 or EP 782707. The assay device and a surface or surfaces of the slot in the reader, into which the assay device is inserted, are so shaped and dimensioned that (1) the assay device can only be successfully inserted into the reader in the appropriate orientation; and (2) there is a precise three dimensional alignment of the reader and an inserted assay device, which ensures that the assay result can be read correctly the reader.

A suitable assay device/reader device combination exhibiting this precise three dimensional alignment is disclosed in EP 833145.

When an assay device is correctly inserted into the reader, a switch is closed which activates the reader from a "dormant" mode, which is the normal state adopted by the reader, thereby reducing energy consumption.

Figure 2:
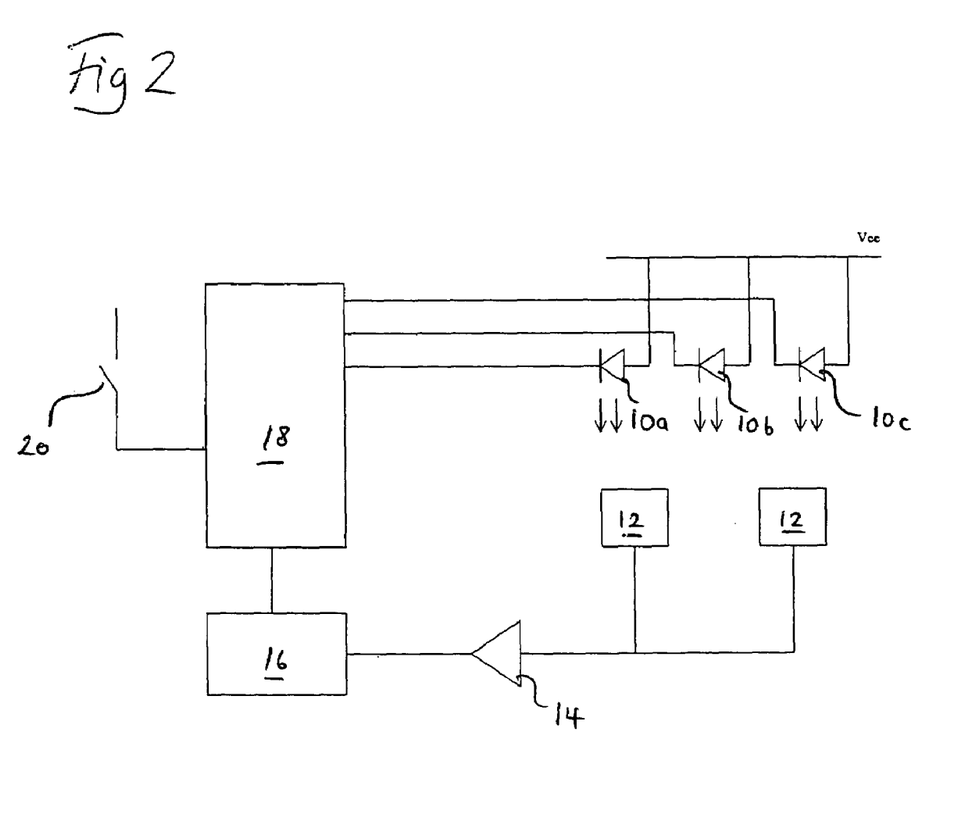
FIG. 2 is a block diagram illustrating schematically some of the internal components of the reading device embodiment depicted in FIG. 1.

Enclosed within the housing of the reader (and therefore not visible in FIG. 1) are a number of further components, illustrated schematically in FIG. 2.

Referring to FIG. 2, the reader comprises three LED's 10*a,b*, and *c*. When a test stick is inserted into the reader, each LED 10 is aligned with a respective zone of the test stick. LED 10*a* is aligned with the test zone, LED 10*b* is aligned with the reference zone and LED 10*c* is aligned with the control zone. Respective photodiodes 12 detect light reflected from the various zones and generate a current, the magnitude of which is proportional to the amount of light incident upon the photodiodes 12. The current is converted into a voltage, buffered by buffer 14 and fed into an analogue to digital converter (ADC, 16). The resulting digital signal is read by microcontroller 18.

In a simple arrangement, a separate photodiode is provided to detect from each zone (i.e. the number of photodiodes equals the number of zones from which reflected light measurements are made). The arrangement illustrated in FIG. 2 is more sophisticated, and preferred. Two photodiodes 12 are provided. One photodiode detects light reflected from the test zone and some of the light reflected from the reference zone. The other photodiode 12 detects some of the light reflected from the reference zone and the light reflected from the control zone. The microcontroller 18 switches on the LED's 10 one at a time, so that only one of the three zones is illuminated at any given time—in this way the signals generated by light reflected from the respective zones can be discriminated on a temporal basis.

FIG. 2 further shows, schematically, the switch 20 which is closed by insertion of an assay device into the reader, and which activates the microcontroller 18. Although not shown in FIG. 2, the device further comprises a power source (typically one or two button cells), and an LCD device responsive to output from the microcontroller 18.

In use, a dry test stick (i.e. prior to contacting the sample) is inserted into the reader, this closes the switch 20 activating the reader device, which then performs an initial calibration. The intensity of light output from different LED's is rarely identical. Similarly, the respective photodetectors are unlikely to have identical sensitivities. Since such variation could affect the assay reading an initial calibration is effected, in which the microcontroller adjusts the length of time that each of the three LED's is illuminated, so that the measured signal from each of the three zones (test, reference and control) is approximately equal and at a suitable operating position in a linear region of the response profile of the system (such that a change in intensity of light reflected from the various zones produces a directly proportional change in signal).

After performing the initial calibration, the device performs a further, finer calibration. This involves taking a measurement ("calibration value") of reflected light intensity for each zone whilst the test stick is dry—subsequent measurements ("test values") are normalised by reference to the calibration value for the respective zones (i.e. normalised value=test value/calibration value).

To conduct an assay, a sample receiving portion of the test stick is contacted with the liquid sample. In this case of a urine sample, the sample receiving portion may be held in a urine stream, or a urine sample collected in a receptacle and the sample receiving portion briefly (for about 5–20 seconds) immersed in the sample. Sampling may be performed whilst the test stick is inserted in the reader or, less preferably, the stick can be briefly removed from the reader for sampling and then reintroduced into the reader.

Measurements of reflected light intensity from one or more (preferably all three) of the zones are then commenced, typically after a specific timed interval following insertion of the test stick into the reader. Desirably the measurements are taken at regular intervals (e.g. at between 1–10 second intervals, preferably at between 1–5 second intervals). The measurements are made as a sequence of many readings over short (10 milliseconds or less) periods of time, interleaved zone by zone, thereby minimising any effects due to variation of ambient light intensity which may penetrate into the interior of the reader housing.

Figure 3:
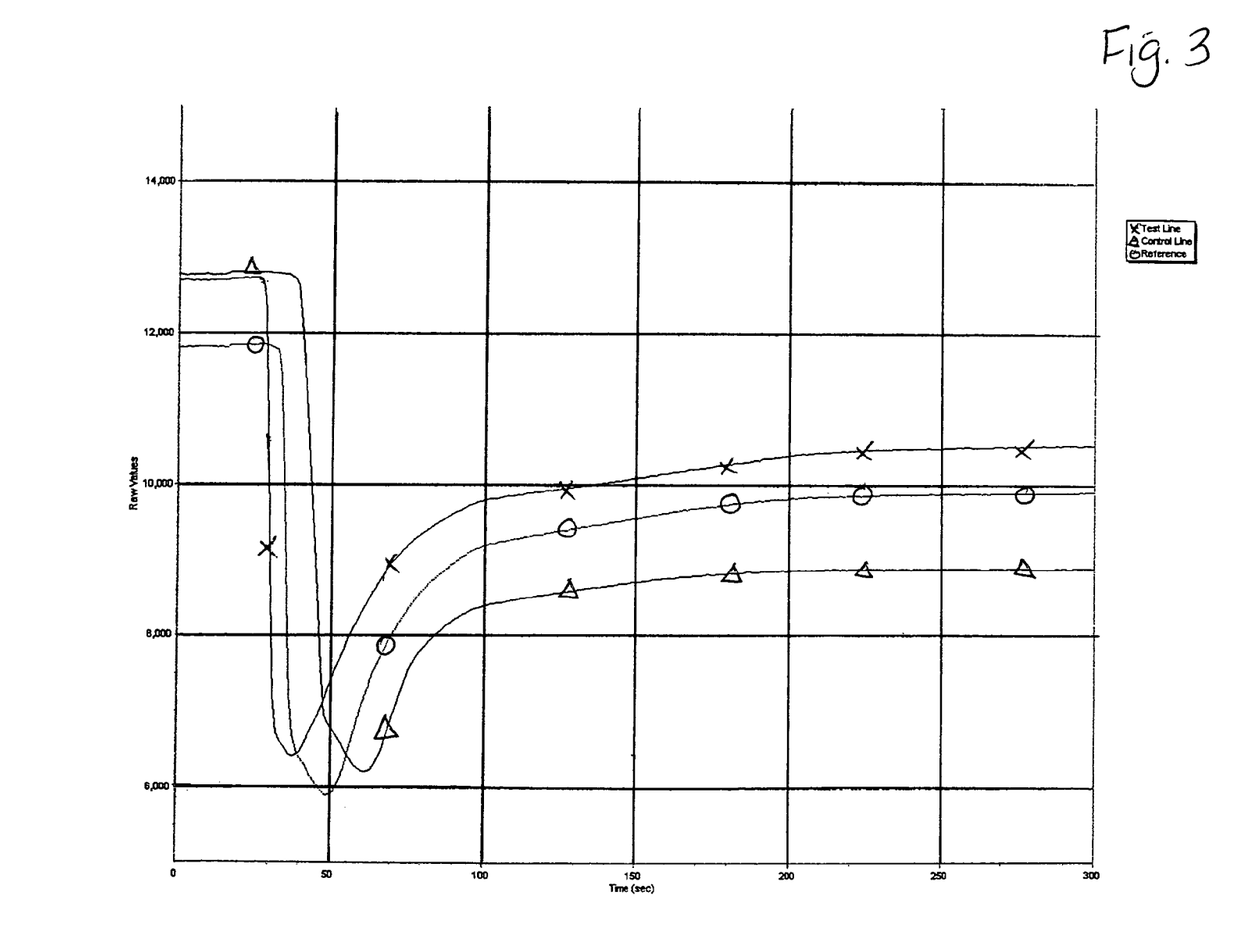
FIGS. 3–5 are graphs showing various signals returned from different portions of a test stick, inserted into the reading device illustrated in FIGS. 1 & 2, and their variation with time.

FIG. 3 is a graph showing the intensity of reflected light (arbitrary values) against time detected from each of the three zones, using a sample which does not contain the analyte of interest. The profile for the test zone is indicated by crosses, that for the reference zone by circles, and that for the control zone by triangles.

Considering the test zone profile, there is an initial lag phase during which the liquid sample is migrating along the porous carrier. In this period, the level of light reflected by the test zone is essentially constant. As the sample reached the test zone the amount of light reflected sharply decreases. This is primarily due to absorption of light by the coloured particulate label transported by the liquid sample. However some of the reduction in reflected light intensity is simply due to wetting of the nitrocellulose porous carrier, since dry nitrocellulose is more reflective.

As the fluid front moves past the test zone the level of reflected light starts to increase, the coloured label being transported with the sample downstream past the test zone. The reflected light intensity does not return to the original level because of the wetting of the nitrocellulose and because a small amount of the coloured particulate label is left behind as the liquid advances.

Generally similar profiles are exhibited by the reference and control zones, although these are downstream of the test zone and so lag further behind. The control zone profile, in particular, does not return to its original level of reflected light intensity because of development of the "control line" (i.e. deposition of coloured particulate label in the control zone).

Figure 4:
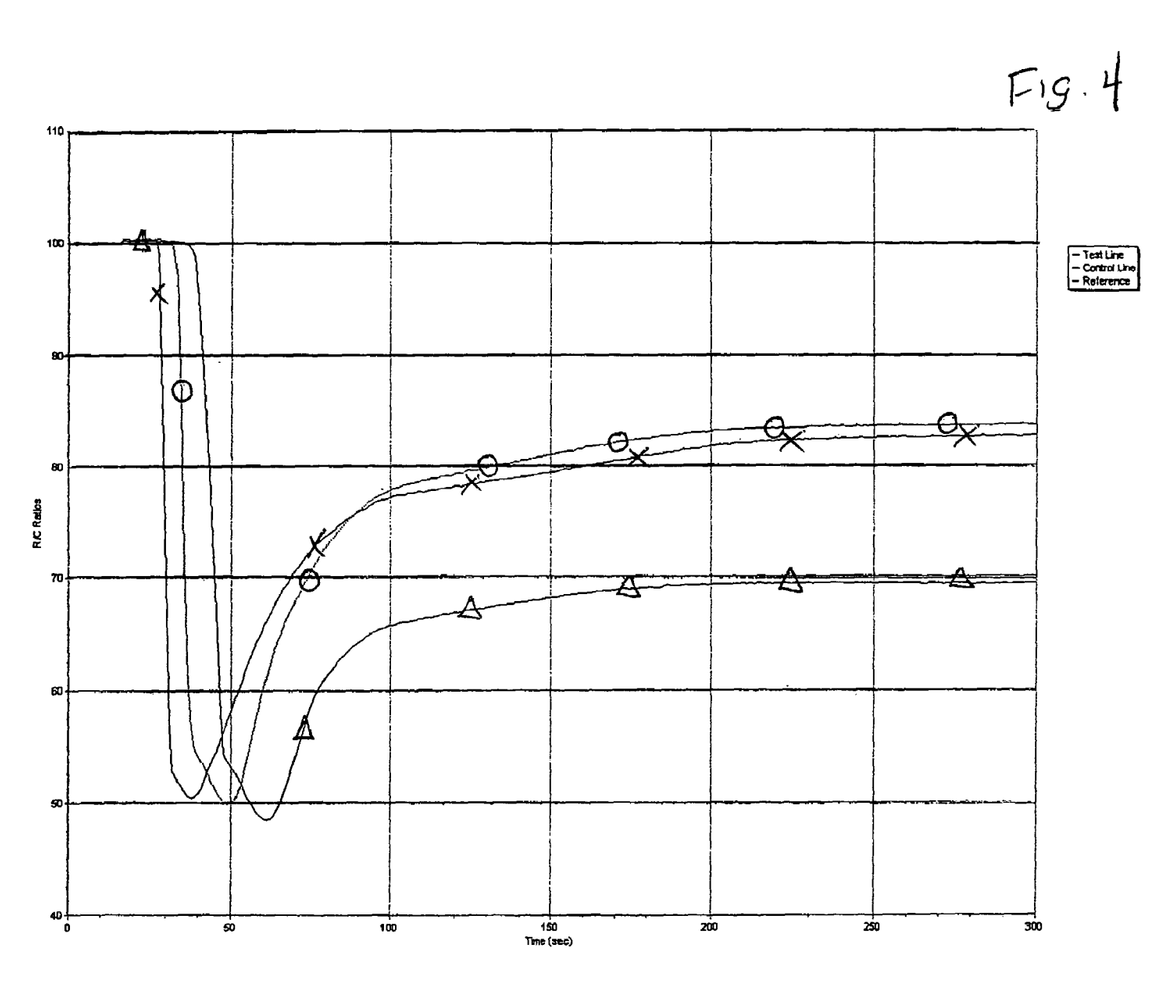

FIG. 4 is essentially similar, and shows the profiles obtained using % normalised results (i.e. test value divided by calibration value×100). The profile being expressed in terms of % of calibration value against time. FIG. 4 demonstrates that normalisation of the test readings against an initial calibration reading reduces the variation in signal from the test, reference and control zones (although again the control zone value remains low due to the deposition of labelled reagent in the control zone).

In order to calculate the flow rate of the liquid sample along the porous carrier, the exemplified reading device actually compares the normalised results from the test and control zones with the result obtained from the reference zone in order to arrive at a "Relative attenuation of reflected light intensity" (% A).

$$\left[ \% A = \frac{(Ref(t)/Ref(\text{cal}) - Test(t)Test(\text{cal})}{Ref(t)/Ref(\text{cal})} \right]$$

Figure 5:
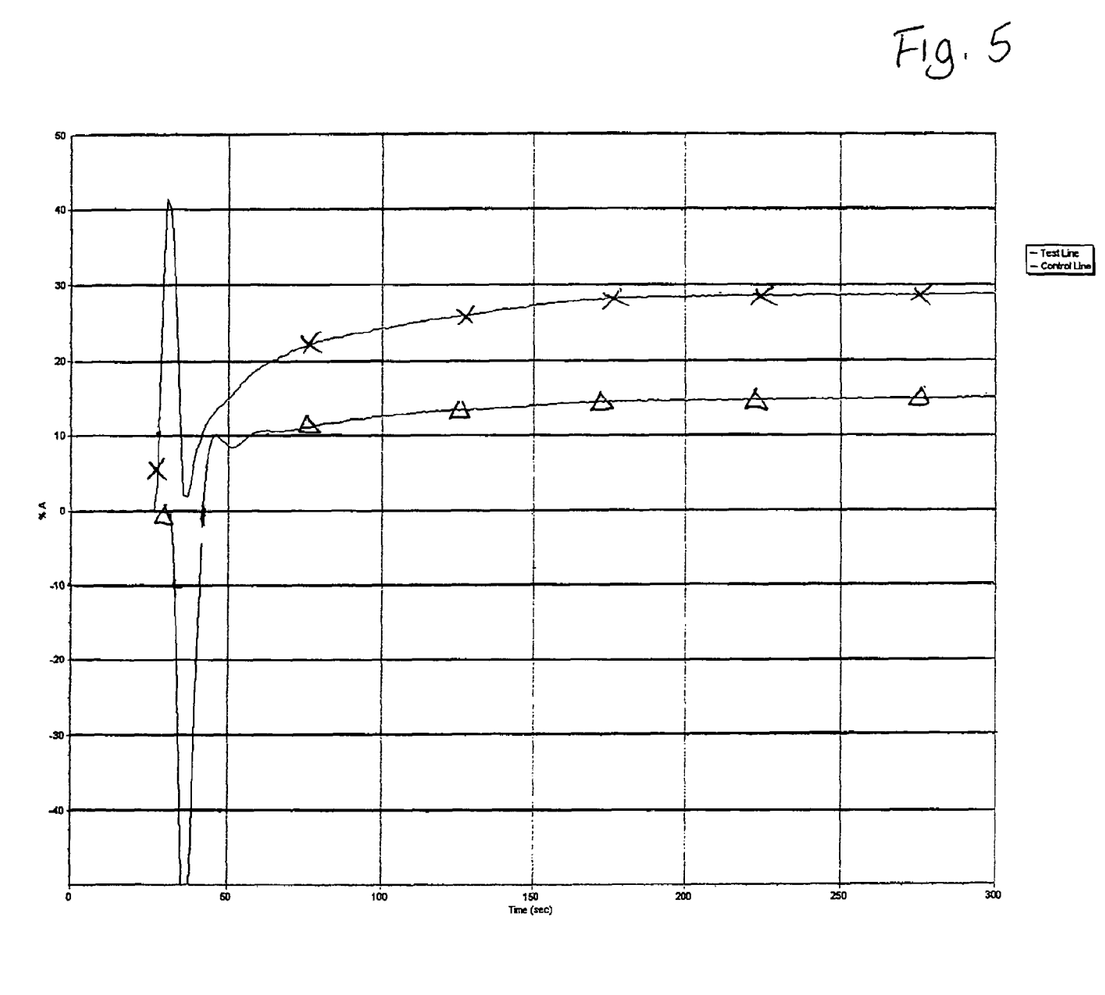

Typical % A profiles (against time), for a sample containing a relevant analyte of interest, are shown in FIG. 5. A positive attenuation means that the zone in question is reflecting less light than the reference zone, whilst a negative attenuation means that the zone in question is reflecting more light than the reference zone.

Referring to the % A profile of the test zone, it is apparent that the test zone signal is initially greatly attenuated (relative to the reference zone) when the liquid sample (with coloured particulate label) reached the test zone, but has not yet reached the reference zone. After about 35 seconds, the liquid sample starts to reach the reference zone and this leads to a sudden drop in the relative attenuation of the test zone. After about 40 seconds, the fluid front starts to leave the reference zone leading to an increase in the reflectivity of the reference zone and therefore an increase in the relative attenuation of the test zone. This levels off and eventually reaches a plateau, at a positive attenuation of just under 30%, the test zone having captured some of the coloured particulate label due to the presence in the sample of the analyte of interest.

Considering the profile for the control zone, it is apparent that there is an initial sharp fall (negative attenuation), since the liquid sample reaches the reference zone before the control zone. As the liquid sample starts to leave the reference zone before the control zone the relative negative attenuation in signal from the control zone starts to return to zero, and as the liquid samples reached the control zone the relative attenuation becomes positive and reached a plateau level of about 15%, due to the deposition of labelled reagent in the control zone to provide a positive control result.

Whilst in the presently exemplified reader the test zone result is compared with the reference zone result, a useful alternative would be to compare the test zone result with the control zone result.

In general terms the flow rate is calculated by detecting the change in reflected light intensity associated with the arrival of the liquid sample at a particular zone, and determining the time which elapses between the arrival of the liquid sample at the various zones. More precisely, the flow rate is calculated as described below.

The signal at all three zones is measured irrespective of the position of liquid on the test strip.

The signal attenuation at the test zone is measured with respect the signal attenuation at the reference zone. When the fluid front arrives at the test zone the signal attenuation will change relative to the reference zone, due to the fluid front not yet having reached the reference zone (it being positioned downstream from the test zone). Timing is commenced when the signal attenuation of the test zone relative to the reference zone is greater than 10%. It should be mentioned that the value of 10% indicates the degree of confidence including any margin of error which has been attached to the measurement reading, which in itself depends on the various measurement parameters, e.g. test strip, optics. This might vary and be chosen to be any convenient value.

The liquid then proceeds into the reference zone and when the signal attenuation of the control zone relative to the reference zone is greater than minus 10% (−10%), the device considers that the liquid has reached the control zone (the minus value reflecting that the control zone is positioned downstream from the test zone). When the signal attenuation of the control zone relative to the reference zone is greater (i.e. more positive) than zero, the device determines that the liquid has reached the control zone. Thus the time measurement by the device may not necessarily exactly correspond to the time when the fluid arrives at the respective zones.

Although in this example the reader measures the rate of passage of liquid between the test and control zones, it measures it with respect to the signal obtained from the reference zone. However the arrival of liquid at the test and control zones could be determined absolutely, (i.e. not by measurement with respect to the reference zone).

The reader is also programmed to declare an assay result invalid if the liquid sample is detected at the control zone before it is detected at the reference zone, as this is indicative that the liquid sample has followed an abnormal flow path.

Example 2

A single set of optics is used to determine both the signal and the flow rate. The maximum and minimum flow rates are set at 5 and 40 s, respectively. Thus any sample that takes longer than 40 s is rejected as being too slow (which may be due to undersampling), any sample that is quicker than 5 s is rejected as being too fast. The flow rate will be influenced by a number of factors including porosity, distance between control and test-lines as well as any chemistry in the porous strip which might modify flow.

Timing is determined and set to zero when the fluid reaches the test-line. The timer is then set and the time for the fluid to reach the control line is measured. As a further control check, the device monitors that the fluid has passed through the reference zone. Additionally as a further control feature, the device also monitors that the fluid has passed through the test, reference and control zones in that order before it will accept a flow rate measurement as authentic, even if it satisfies the flow rate range of between 5 and 40 s.

In other embodiments, of course, the upper and lower flow rate limits can be set to a wide variety of values, in accordance with particular properties of test fluids and/or with the factors described above.

Example 3

An assay result reader according to the present disclosure may also include a system for declaring the result of an assay before completion of the assay, if a analyte measurement signal is above an upper threshold or below a lower threshold. Such systems are described in U.S. patent application Ser. No. 10/741,416, filed Dec. 19, 2003.

Example 4

An assay result reader according to the present disclosure may also include optical arrangement such as those described in U.S. patent application Ser. No. 60/508,001, filed Oct. 2,2003.

Figure 6:
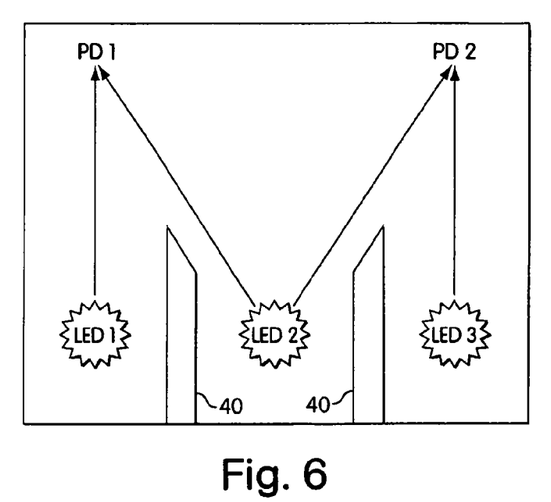
FIGS. 6–8 are schematic representations of an embodiment incorporating a preferred light source/photodetector arrangement.
Figure 7:
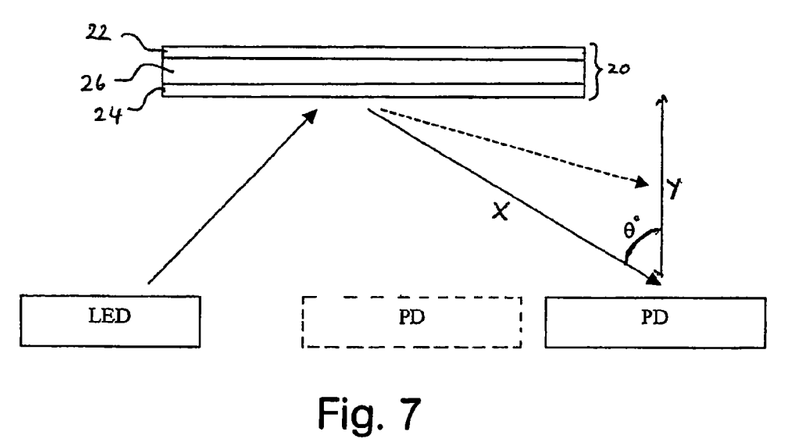
Figure 8:
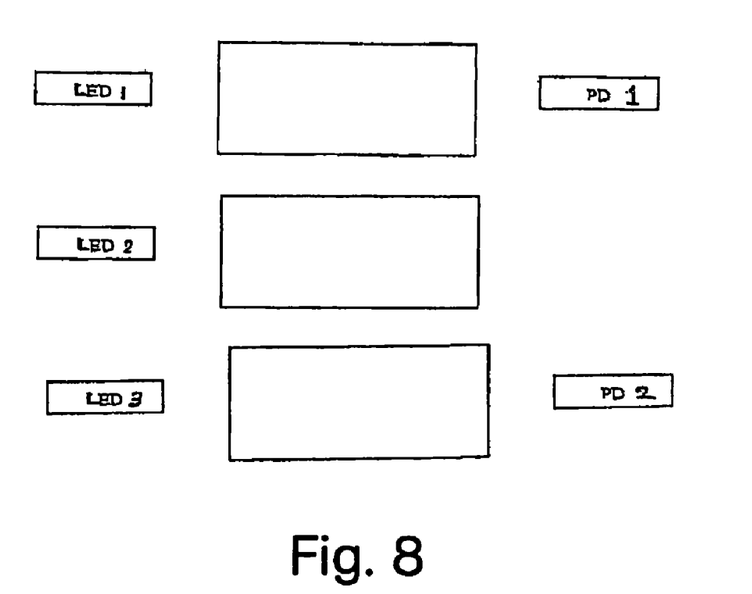

FIG. 6 is a schematic representation of the layout of the 3 LED/2 Photodiode optical system described in Example 1. FIG. 7 is a schema representation of a side elevation of one LED/Photodiode, and illustrating their position relative to a nitrocellulose test strip. FIG. 8 is a schematic plan view of the LED/Photodiode arrangement, again illustrating their position relative to a test strip.

Referring to FIG. 6, an optics block component for accommodation within an assay result reading device may include three LEDs (LED 1, 2 and 3) and two photo detectors (PD1 and PD2). Light from LED 1 illuminates a test zone of a test strip (not shown) inserted into the reader. Light reflected from the test zone is detected by PD1. Light from LED3 illuminates a control zone of the test strip and light reflected therefrom is detected by PD2. Light from LED2 illuminates a reference zone of the test strip.

Each LED is optically isolated by light-impermeable baffles 40, which ensure that the various LEDs are capable of illuminating only its respective zone of the test strip. However the surfaces of the baffles facing LED2 are angled so as to allow LED2 to illuminate a slightly wider portion of the test strip than LED1 or 3, and this in turn allows light reflected from the reference zone to be detected by both PD1 and PD2.

The relative positioning of the test strip, LEDs and photodiodes may be better understood by reference to FIGS. 7 and 8.

Referring to FIG. 7, a test strip 20 is inserted into the reading device above the plane of the LEDs and photodiodes. The test strip 20 is of laminate construction including an uppermost backing layer 22 of reflective opaque white MYLAR®, a synthetic plastics material, and a lowermost front layer 24 of clear MYLAR®. Sandwiched between the MYLAR® layers 22, 24 is a layer of porous material 26 (typically nitrocellulose). The purpose of the MYLAR®layers is to protect the delicate nitrocellulose and provide mechanical strength and rigidity. In addition, the opaque backing layer 22 is relatively highly reflective, and this serves to improve contrast: relatively little light is absorbed by the layers 24, 26 and much of the light incident upon the various zones would therefore tend to pass straight through the test strip, but the reflective MYLAR® backing layer 22 ensures that this light is reflected. In addition, since the particulate label accumulating in the nitrocellulose layer 26 absorbs only a portion of the light as it passes through in a generally upwards direction, the label has in effect a second chance to absorb light as it passes back through the test strip 20 in a generally downwards direction, having been reflected by the opaque MYLAR® backing layer 22. This significantly improves the signal-to-noise ratio.

As can be seen from FIGS. 7 and 8, the photodiodes PD1 and PD2 are aligned with their respective LEDs, LED1 and 3, but are offset, in that the LEDs lie towards one side of the test strip while the photodiodes lie towards the other side. Having the photodiodes offset in this way avoids, or at least reduces, the amount of specular reflection from the clear MYLAR® layer 24 detected by the photodiodes (i.e. light which is reflected directly from the initial MYLAR® layer 24 without ever penetrating into the nitrocellulose layer— detection of such reflections would decrease the signal: noise ratio).

Referring to FIG. 7 the relationship between signal intensity (I) and the angle ($\theta$) of the reflected light relative to the photodiode is $I \propto \cos \theta^4$. Furthermore, the relationship between signal intensity (I) and the distance (x) of the photodiode from the reflecting object is $I \propto 1/x^2$ (i.e. the inverse square law). It is apparent that, in view of the inverse square law, it would generally be preferred to position the photodiodcs as close as possible to the test strip (i.e. decrease x), so as to increase the signal intensity I. However, merely decreasing the vertical separation y between the photodiode and the test strip would increase angle $\theta$, decreasing the value of $\cos \theta$ and therefore tend to reduce the signal intensity.

An alternative approach to improve signal intensity would be to re-position the photodiode nearer the center of the system (indicated by the dotted lines in FIG. 7) which would simultaneously decrease x and $\theta$. However, this is found to be undesirable as it increases the likelihood of detecting specular reflections. Accordingly an aligned but offset position for the photodiodes provides an optimal compromise of the considerations.

It may be noted from FIG. 8 that photodiode 1 is aligned with the test zone and photodiode 2 is aligned with the control zone. This alignment ensures that any variation of the relative positioning of the test strip and assay reader has minimal effect on the angle θ. While PD1 and PD2 are not aligned with the reference zone, and are therefore subject to a relatively large (and therefore undesirable) angle of θ, this problem is not significant because (i) the use of two detectors to read the reference zone allows for compensation of any positional variation, since relative movement of the test strip so as to increase θ for one photodetector may decrease θ for the other photodetector; and (ii) the reference zone is used to give a background reading for calibration purposes—the photodiodes are not required to measure the signal intensity from a narrow line (as with the test or control zones), and so the measurement of the reference zone signal is inherently less sensitive to variation from mis-positioning.

All patents and patent applications referred to in this disclosure are hereby incorporated herein in their entireties by this reference.

The invention claimed is:

1. An assay result reading device for reading the result of an assay performed using a liquid transport carrier, the device comprising:
   at least one light source capable of emitting light incident upon at least one of two or more spatially separated zones of the carrier;
   a photodetector so positioned as to be capable of detecting light emanating from each of the two said zones and generating signals representing the presence or absence of a fluid sample in the respective zone; and
   a computation circuit responsive to the signals to:
   calculate a flow rate for a fluid flowing along the carrier;
   compare the calculated flow rate to upper and lower limits; and
   reject the assay result if the calculated flow rate is outside the upper and lower limits.

2. A device according to claim 1, wherein the carrier comprises a porous carrier.

3. A device according to claim 1, wherein the at least one light source comprises a light emitting diode.

4. A device according to claim 1, wherein the at least one photodetector comprises a photodiode.

5. A device according to claim 1, wherein the at least one light source comprises at least two light sources, and the at least one photodetector comprises at least two photodetectors.

6. A device according to claim 5, wherein:
   the first light source is capable of emitting light incident on the first zone, and the first photodetector detects light emanating from the first zone; and
   the second light source is capable of emitting light incident on the second zone, and the second photodetector detects light emanating from the second zone.

7. A device according to claim 1, wherein the at least one light source comprises at least two light emitting diodes, and the at least one photodetector comprises at least two photodiodes.

8. A device according to claim 1, wherein the signal representing the presence or absence of a fluid sample in a zone is calculated based upon the optical reflectance, the transmissivity, or both, of the carrier.

9. A device according to claim 1, further comprising a housing enclosing the at least one light source and the at least one photodetector.

10. A device according to claim 9, wherein the housing is about 12 cm long or less, about 2.5 cm wide or less, and about 2.2 cm tall or less.

11. A device according to claim 1, wherein the at least one light source and the at least one photodetector are disposed within an area of about 1 square centimeter or less.

12. A device according to claim 1, wherein the at least one light source and the at least one photodetector are disposed within an area of about 0.7 square centimeters or less.

13. A device according to claim 1, wherein signals generated by the at least one photodetector represent an amount of analyte present in a zone.

14. The device according to claim 10, wherein the housing is about 12 cm long, about 2.5 cm wide, or about 2.2 cm tall.

15. A method of performing an assay for an analyte of interest in a liquid sample, the method comprising:
   positioning a liquid transport carrier in relation to an assay result reader, the carrier having at least two spatially-separated zones, the reader comprising a housing enclosing at least one light source and at least one photodetector, and the carrier positioned so that the at least one light source emits light incident on at least one of the zones, and so that light emanating from at least one of the zones is incident on the photodetector;
   applying or introducing the liquid sample to the liquid transport carrier;
   calculating a flow rate of the liquid sample along the carrier in response to signals generated by the at least one photodetector representing the presence or absence of the liquid sample in a respective zone;
   determining whether the calculated flow rate is within predetermined acceptable limits; and
   performing at least one additional action based on the determination.

16. A method according to claim 15, wherein the additional action comprises rejecting an assay result if the calculated flow rate is not within the predetermined acceptable limits.

17. A method according to claim 15, wherein the liquid transport carrier is positioned at least partly inside the assay result reader.

18. A method according to claim 15, wherein the assay result reader further comprises a second photodetector, the at least one light source comprises first and second, and third light sources, the liquid transport carrier has three spatially separated zones, and wherein:
   each light source is aligned with and laterally offset from a corresponding liquid transport carrier zone;
   the first photodetector is so positioned as to receive light emanating from the first zone and the second zone; and
   the second photodetector is so positioned as to receive light emanating from the second zone and the third zone.

19. A device, comprising:
   a housing;
   a liquid transport carrier in a test position with respect to the housing, the liquid transport carrier being configured to support flow of a liquid applied to a sample application zone of the liquid transport carrier to at least first and second spaced-apart zones of the liquid transport carrier;
   a light source system configured to selectively illuminate each of the first and second spaced-apart zones of the liquid transport carrier;
   a light detection system configured to detect light from the first zone of the liquid transport carrier when the first zone is illuminated by the light source, (b) detect light from the second zone of the liquid transport carrier when the second zone is illuminated by the light source, and (c) output signals indicative of the light detected from the first and second zones; and a processor configured to determine a flow rate of liquid along the liquid transport carrier based at least in part on the signals indicative of the light detected from the first and second zones.

20. The device of claim 19, wherein the light source system comprises a first light source to illuminate the first zone of a liquid transport carrier and a second different light source to illuminate the second zone of a liquid transport carrier and the light detection system comprises a first detector to detect light from the illuminated first zone and a second different detector to detect light from the illuminated second zone.

21. A method, comprising:

illuminating a first zone of a liquid transport carrier with light, the liquid transport carrier being at least partially enclosed within a housing, at least a first portion of the liquid transport carrier being wet with a liquid;

detecting light from the first zone of the liquid transport carrier;

illuminating a second zone of the liquid transport carrier with light, the second zone being spaced apart from the first zone;

detecting light from the second zone of the liquid transport carrier;

determining a flow rate of the liquid along the liquid transport carrier based at least in part on the light detected from the first zone and the light detected on the second zone; and performing at least one additional action based on the determined flow rate.

22. The method of claim 21, wherein a first light source is used to illuminate the first zone and a second different light source is used to illuminate the second zone.

23. The method of claim 22, wherein a first detector is used to detect light from the illuminated first zone and a second different detector is used to detect light from the illuminated second zone.

24. A device, comprising:

a housing;

a porous test strip disposed in a test position with respect to the housing, the test strip comprising a sample receiving zone located external to the housing and first and second zones located within the housing, the sample receiving zone, the first zone, and the second zone being spaced apart from one another along a flow path defined by the test strip;

a light source system configured to illuminate the first zone and the second zone of the test strip;

a light detection system configured to detect light from the first zone of the test strip when the first zone is illuminated by the light source, output a first signal indicative of light detected from the first zone, detect light from the second zone of the test strip when the second zone is illuminated by the light source, and output a second signal indicative of light detected from the second zone; and a processor configured to receive the first and second signals and, based at least in part on the first and second signals, determine a result indicative of a time required for a liquid received by the sample receiving zone to flow from the first zone along the flow path to the second zone.

25. The device of claim 24, wherein the device is configured to determine the presence of an analyte in the liquid received by the sample receiving zone.

26. A method, comprising:

allowing a liquid to advance from a sample receiving zone to a first zone and subsequently to a second zone of a porous test strip after the liquid had been received by the sample receiving zone, the sample receiving zone being located external of a housing, the first and second zones being located internal of the housing, the sample receiving zone, the first zone and the second zone being spaced apart from one another along the porous test strip;

illuminating the first zone of the test strip with light from a first light source;

detecting light from the illuminated first zone using a light detection system;

providing to a processor a first electronic signal indicative of the light detected from the first zone, illuminating the second zone of the test strip with light from a second light source;

detecting light from the illuminated second zone using the light detection system;

providing to the processor a second electronic signal indicative of the light detected from the second zone;

determining, based at least in part on the first and second electronic signals received by the processor, a result indicative of the time required for the liquid received by the sample receiving zone to flow from the first zone to the second zone; and performing at least one additional action based on the determined result.

27. The method of claim 26 further comprising determining the presence of an analyte in the liquid, and outputting a value indicative of the presence of the analyte.

* * * * *